United States Patent [19]

Johansson et al.

[11] Patent Number: 4,715,911
[45] Date of Patent: Dec. 29, 1987

[54] METHOD FOR THE PRODUCTION OF A PLASTIC CONTAINER

[75] Inventors: Arne Johansson, Roskilde; Erland Namensen, Lejre, both of Denmark

[73] Assignee: A/S Nunc, Roskilde, Denmark

[21] Appl. No.: 843,685

[22] Filed: Mar. 25, 1986

[30] Foreign Application Priority Data

Mar. 25, 1985 [DK] Denmark ............................ 1345/85

[51] Int. Cl.⁴ .............................................. B32B 31/20
[52] U.S. Cl. ...................................... 156/69; 156/73.1; 156/73.6; 220/359
[58] Field of Search ........................ 156/69, 73.1, 73.6; 220/359

[56] References Cited

U.S. PATENT DOCUMENTS 3,824,138  7/1974  Karobath et al. ............. 156/73.1 X
4,259,419  3/1981  Uba et al. ........................ 156/73.1 X
4,659,405  4/1987  Walter .................................... 156/69

Primary Examiner—Robert A. Dawson
Attorney, Agent, or Firm—Watson, Cole, Grindle & Watson

[57] ABSTRACT

A method for the production of a plastic container which includes an essentially planar base part and a detachable top part comprises placing a top part having a thin flange extending from an end face at an open end thereof on an essentially planar base part, vibrating the top part relative to the base part to melt the thin flange, and discontinuing the vibration before the thin flange has become completely molten. The resulting plastic container is both air- and liquid-proof, yet the top part is easily detachable from the base part.

6 Claims, 4 Drawing Figures

METHOD FOR THE PRODUCTION OF A PLASTIC CONTAINER

BACKGROUND OF THE INVENTION

This invention relates to the production of a plastic container comprising an essentially planar base part and a detachable top part attached thereto, the top part comprising at least one compartment.

More particularly, the invention relates to a plastic container comprising a top part which is closed at its upper end and which has a sealable opening provided in the side wall of the top part, and a transparent base part, such that the base part after the removal of the top part from the base is suitable for use as a slide under a microscope.

Containers of the above-mentioned type find widespread use in the cultivation of cells and the subsequent investigation of the cell cultures formed.

Before a cell cultivation is started, a culture medium is introduced into the container through the opening in the side wall of the top part, and the culture medium is caused to form a uniform layer on the top surface of the planar base part. Subsequently, the cells are introduced into the container, which is then sealed and incubated for a certain period under suitable temperature conditions so as to form a cell layer on the base part.

The investigation of the cell layer thus formed is effected after removal of the top part from the base part and by placing the planar base part with the cell layer thereon under a microscope, the base acting as a slide.

Prior to the investigation of the cell layer under the microscope, the cell layer may be dyed or subjected to another pretreatment, if desired.

The plastic container should preferably be sealed during the cultivation in order to prevent undesired substances from entering into the container and culture medium, or to prevent cells or substances formed during the cultivation from leaving the container. In this connection it should be mentioned that the pressure within the container may raise somewhat during the cultivation phase.

On the other hand, the top part should be easily detachable from the base part when the cultivation is completed and the investigation is to be started.

Danish patent specification No. 133164 discloses a cultivation container of the above-mentioned type. This prior art container consists of a top part comprising several compartments, the top part being placed on the top surface of a planar base part, the zones located between the lower edges of the top part and the base part being sealed with a liquid-proof adhesive, such as a microcrystalline wax or an organopolysiloxane elastomer, which is introduced into these zones by injection through channels formed in the top part and opening into grooves provided on the lower edges.

The provision of these channels and grooves in the top part complicates the production of the prior art plastic container and furthermore, the prior art plastic container suffers from the defect that the injected adhesive tends to be non-uniformly distributed in the grooves, so that the container will not obtain the required tightness. Additionally, the prior art container tends to leak when the pressure within the container increases.

The object of the present invention is to provide a plastic container which is liquid-proof under normal culturing conditions and from which the top part can be easily removed after cultivation so as to allow the plane base to be used as a slide under a microscope.

SUMMARY OF THE INVENTION

This object is achieved by the method of the invention which comprises the steps of contacting a top part which is open at one end and which at the open end comprises an essentially planar end face with a thin flange projecting from the end face and extending continuously over the full periphery of the compartment(s) in the top part, with an essentially planar base part, vibrating the top part or the base part relative to the other part to partially melt the thin flange and stopping the vibration before the thin flange material has been completely molten.

The invention is based on the discovery that, if the heating caused by the vibration is stopped before the thin flange has been completely molten, a welded joint is formed which is both air- and liquid-proof and which has a sufficiently high mechanical strength to allow the container formed to be used for culturing purposes and on the other hand is so weak that it breaks when the top part manually is forced away from the base part, thus leaving a planar base part suitable for use for investigation purposes.

When used in the combination "thin flange", the word "thin" means tht the flange has a significantly smaller thickness than the wall from which it is projecting, such that the energy generated by the vibration primarily will be concentrated within the flange.

When the method of the invention is utilized for the production of a container for cell cultivation and the base part is to be used for the investigation of the cell culture under a microscope, the thin flange preferably is of a triangular cross-sectional shape and may have a height of about 0.8 mm and a width at the end face of the top part of about 0.3 mm.

These dimensions, however, depend among others on the size of the container and the plastic material used. The thin flange may have another cross-sectional shape than a triangular one.

The vibration is preferably generated with an ultrasonic generator and in practice it is preferred to fix the planar base part and to make the top part vibrate relative to the fixed planar base part.

The melting of the thin flange is controlled by variation of the effect of the ultrasonic generator, the pressure exerted by the top part of the base part and the duration of the ultrasonic welding.

DESCRIPTION OF THE PREFERRED EMBODIMENTS

Figure 1:
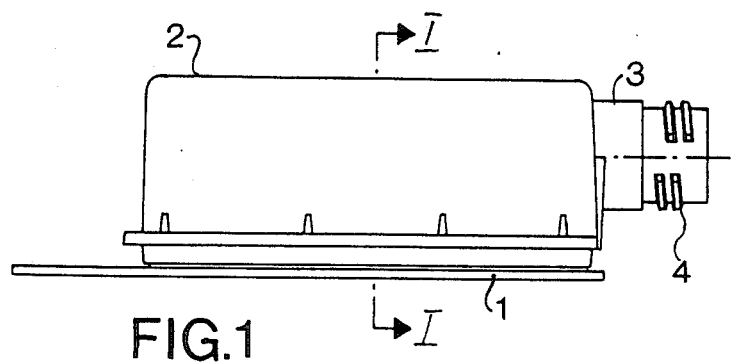
FIG. 1 shows a side view of a plastic container prepared by the method according to the invention.

The plastic container shown in the drawings includes an essentially planar base part 1 which is welded to a top part 2. The latter comprises a pipe section 3 with an external threading 4 for fixing a screw cap, not shown, to the pipe section 3.

Figure 2:
FIG. 2 shows a cross-sectional view of a planar base part for the production of a plastic container according to FIG. 1, shown on an enlarged scale.

As will appear from FIG. 2, the top surface of the base part 1 has a raised part 5 of such dimensions as regards length and width that after welding to the base part, the top part 2 contacts the edges of the raised part 5. The bottom surface of the base part has a recess 6 surrounded by an edge zone 7 which prevents the central part of the bottom surface of the base part from contacting the support on which the container is placed.

Figure 3:
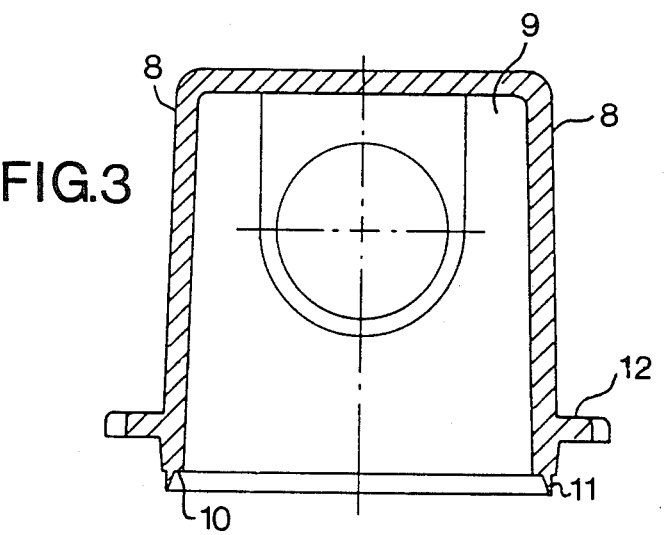
FIG. 3 shows a cross-sectional view of a top part for the production of a plastic container according to FIG. 1, shown on an enlarged scale.
Figure 4:
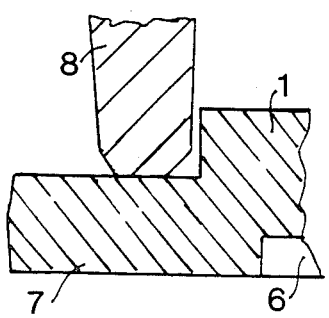
FIG. 4 shows a part of a cross-sectional view taken along the line I—I of the plastic container according to FIG. 1.

The top part 2, which is shown in detail in FIG. 3, includes two side walls 8 and two end walls 9. The walls 8,9 have coplanar end faces 10 with a thin flange 11 extending continuously over the full periphery of the compartment formed between the walls 8,9. Located a short distance from the end face 10 the top part comprises a flange 12 projecting from it on both sides and at the end opposite to the end with the pipe section 3.

When preparing the container shown in FIG. 1, the base part 1 is maintained in contact with the top part 2 in such a position tht the interior surfaces of the side walls 8 and the end walls 9 of the top part are located adjacent to the edges of the raised part 5 of the base part 1. The top part 2 is then caused to vibrate relative to the fixed base part by means of an ultrasonic generator until a partial melting of the thin flange 11 is effected along the full periphery of the top part 2.

As a result of such melting a welded joint is formed which is air and liquid-proof and which is at the same time easy to break when it is desired to release the top part 2 from the base part 1.

What is claimed is:

1. A method of producing a plastic container which includes a base part and an integral top part, the base part and the integral top part being easily separated, said method comprising the steps of
    (a) providing a plastic and essentially planar base part,
    (b) providing a plastic top part which defines at least one compartment therein and an open end, said top part having an essentially planar end face at said open end and a thin flange which projects outwardly from around the entire periphery of said end face,
    (c) positioning said top part and said base part together so that said thin flange of said top part contacts said base,
    (d) vibrating one of said top part and said base part relative to the other part to partially melt said thin flange,
    (e) discontinuing said vibrating before said thin flange becomes completely molten, and
    (f) allowing said flange to cool, such that said top and base parts become attached, thereby producing said plastic container.

2. A method according to claim 1, wherein said thin flange of said top part provided in step (b) has a triangular cross-sectional shape.

3. A method according to claim 6, wherein in step (d) one of said top and base parts is subjected to ultrasonic waves.

4. A method according to claim 6, wherein in step (d) said base part is fixed in position and wherein said top part is vibrated relative to said base part.

5. A method according to claim 6, wherein said base part provided in step (a) has a centrally located raised part having a contour corresponding to the inner contour of the thin flange of said top part.

6. A method according to claim 1, wherein said base part provided in step (a) is formed of transparent plastic.

* * * * *